United States Patent
Krueger et al.

(10) Patent No.: US 8,983,575 B2
(45) Date of Patent: Mar. 17, 2015

(54) DEVICE AND METHOD FOR THE DETERMINATION OF THE POSITION OF A CATHETER IN A VASCULAR SYSTEM

(75) Inventors: Sascha Krueger, Hamburg (DE); Holger Timinger, Hamburg (DE); Joerg Sabczynski, Norderstedt (DE); Joern Borgert, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 1791 days.

(21) Appl. No.: 10/597,984

(22) PCT Filed: Feb. 18, 2005

(86) PCT No.: PCT/IB2005/050467
§ 371 (c)(1),
(2), (4) Date: Aug. 14, 2008

(87) PCT Pub. No.: WO2005/082246
PCT Pub. Date: Sep. 9, 2005

(65) Prior Publication Data
US 2008/0294034 A1    Nov. 27, 2008

(30) Foreign Application Priority Data

Feb. 18, 2004 (EP) .................................... 04100640

(51) Int. Cl.
*A61B 5/05* (2006.01)
*A61B 5/06* (2006.01)
*A61B 19/00* (2006.01)
*A61B 6/12* (2006.01)

(52) U.S. Cl.
CPC . *A61B 5/06* (2013.01); *A61B 19/52* (2013.01); *A61B 19/5244* (2013.01); *A61B 6/12* (2013.01); *A61B 2019/5251* (2013.01); *A61B 2019/5458* (2013.01)
USPC ........................................................... 600/424

(58) Field of Classification Search
USPC ............................ 600/424, 427; 33/424, 427
See application file for complete search history.

(56) References Cited

U.S. PATENT DOCUMENTS

| 5,042,486 | A | 8/1991 | Pfeiler et al. |
| 6,192,144 | B1 | 2/2001 | Holz |
| 6,198,963 | B1 * | 3/2001 | Haim et al. ............... 600/424 |
| 6,266,551 | B1 * | 7/2001 | Osadchy et al. .......... 600/424 |
| 6,266,552 | B1 | 7/2001 | Slettenmark |

(Continued)

FOREIGN PATENT DOCUMENTS

EP    1174082 A    1/2002

*Primary Examiner* — Christopher Cook

(57) ABSTRACT

The invention relates to a device and a method for the determination of the position of a catheter in a vascular system (8). In this, the measured positions ($r_1$, $r_2$) of two magnetic localizers at the tip of a catheter are displaced by correction vectors ($k_1$, $k_2$) while optimizing a quality dimension. The quality dimension includes a component taking account both of the deviation of the measured positions ($r_1$, $r_2$) from the vascular layout and of the deviation of the associated orientation ($r_2 - r_1$) from the orientation of the vascular layout according to a vascular map. In addition, the quality dimension may include components which evaluate the measured shape of the catheter compared to the vascular map. An additional correction step can further ensure that the corrected positions ($r_1'$, $r_2''$) correspond to the preset fixed distance (d) of the localizers (4, 5).

9 Claims, 1 Drawing Sheet

(56) References Cited

U.S. PATENT DOCUMENTS

| | | |
|---|---|---|
| 6,813,512 B2 | 11/2004 | Aldefeld |
| 6,892,090 B2 * | 5/2005 | Verard et al. .................. 600/424 |
| 7,366,562 B2 * | 4/2008 | Dukesherer et al. .......... 600/424 |
| 2004/0249266 A1 * | 12/2004 | Friedrich et al. .............. 600/424 |
| 2005/0065434 A1 * | 3/2005 | Bavaro et al. ................. 600/424 |

* cited by examiner

DEVICE AND METHOD FOR THE DETERMINATION OF THE POSITION OF A CATHETER IN A VASCULAR SYSTEM

The invention relates to a device and a method for the determination of the position of an instrument, in particular of a catheter, in a vascular system with the aid of localizers attached to the instrument.

The success of medical interventions involving the introduction of a catheter into the vascular system of a patient requires a precise knowledge of the actual catheter position relative to the vascular layout. Though this knowledge could in principle be obtained by continuous X-ray fluoroscopic observation using contrast agents, this process cannot be used in view of the exposure of the patient. For this reason, in many cases pre-produced 2D or 3D vascular maps in which the catheter position measured by means of localizing devices is entered are used. In this context, a method is known from U.S. Pat. No. 5,042,486 wherein the position of a localizer at the tip of a catheter is measured by a magnetic localizing device and entered into a static vascular map.

A problem of the known methods, however, lies in the fact that this transfer is not sufficiently accurate, in particular with regard to highly branched and/or circumflex blood vessels, such as coronary vessels. Magnetic localizing devices are further subject to the problem of being affected by external magnetic fields or magnetically active or electrically conductive materials, which are often found in catheter laboratories.

In view of the above background, it is an object of the present invention to provide means for the more accurate determination of the position of an instrument such as a catheter in a vascular system.

This problem is solved by a device and by a method with the features and embodiments as described herein.

The device according to the invention is used to determine the position of an instrument such as a catheter in a vascular system. The term "vascular system" should in the present context be understood as a general term for a network of paths in which the instrument may be located. The instrument could, for instance, be a probe in the gastrointestinal tract or in a technical environment (e.g. within a machine). The fact that the system of blood vessels is hereinafter primarily used as an example for a vascular system should not limit the scope of the invention.

The device comprises the following components:

One or more localizers fitted to the instrument, the spatial position of which can be measured. In addition, the orientation and/or shape of an instrument section is to be measured by means of the localizer(s). In practically important cases, at least two localizers, the spatial position of which can be measured, are provided, and the orientation of the instrument section between the localizers can be calculated by subtraction. However, even a single localizer can supply information both on its position and on its orientation—and thus on the orientation of the associated instrument section. For the at least approximate determination of the shape of an instrument section, several localizers are required as a rule, their measured positions representing, for instance, reference points for a model of the instrument's layout. The types of localizers are not subject to any a priori restrictions. They may, for instance, be markers impermeable to X-rays, which can be located on an X-ray image. Preferred are so-called active localizers (in particular non-line-of-sight sensors) permitting position detection independent of any imaging devices.

A data processing unit with a memory in which a vascular map is stored. The term "vascular map" denotes a representation or diagram of the layout of the vessels in the relevant area; this vascular map may, for instance, be produced by angiographic X-ray photography prior to an operation. The vascular map is typically two- or three-dimensional.

The data processing unit is further set up to correct measured spatial positions of the at least one localizer, taking into account the vascular map and a predetermined quality dimension (i.e. minimized or maximized depending on the definition of the quality dimension). The above quality dimension includes at least two weighted components, the first component measuring the deviation of the measured position of the localizer from the vascular layout as represented by the vascular map and the second component measuring the deviation of the measured orientation and/or shape of the instrument section from the vascular layout as represented by the vascular map.

A device of the type described above has been found to offer, in particular in the case of highly branched and/or circumflex vessel layouts, such as prevalent in coronary vessels, a high degree of correspondence between the corrected positions of the localizers and their actual positions in the vascular system. In particular, the device can offer good compensation for motion artifacts caused by differences between a vascular map and the actual vascular layout due to bodily movements (in particular movement and breathing of the patient). This positive result is essentially due to the fact that the distance of the measured position from a vascular layout according to a vascular map is minimized while at the same time the measured orientation and/or shape of the associated instrument section is compared to the orientation and/or shape of the vessels.

According to a preferred embodiment of the device, at least one of the localizers is a magnetic field sensor forming part of an electromagnetic localizing device. In electromagnetic localizing devices, field generators generate a magnetic field inhomogeneous in space and/or time, wherein the value and direction of the field strength can be measured by magnetic field sensors, allowing conclusions to be drawn regarding the relative position and orientation of sensor and field generator. Said localizing devices are, however, easily affected by external magnetic fields, which are frequently generated in catheter laboratories by the equipment located there. In many cases, however, this interference varies on a relatively large length scale, so that it can be considered as approximately constant locally. As a result, two localizers located at a small distance from one another are subject to the same interference. While the absolute position of the localizers is now subject to a correspondingly large error, the interference is virtually canceled out when calculating the orientation of the localizers from the position difference, enabling their orientation to be measured with relatively high accuracy. The consideration of the orientation of the localizers or of the orientation/shape of an instrument section in the quality dimension is therefore based on precisely measurable information.

According to another further aspect, the data processing unit is set up to calculate a locally continuous transformation from the point-by-point corrections. This means that individual correction vectors are considered as reference points for interpolating or extrapolating a transformation map. By means of this transformation, a correction relative to the vascular map can be calculated for virtually any point in a covered area. The transformation map can further be refreshed with any newly calculated correction vector and is therefore continually updated.

According to a preferred embodiment of the invention, at least two localizers are attached to the instrument in a known mutual relative position. The spacing of two localizers, in particular, can be predetermined and held constant by attaching the localizers for instance to different ends of a rigid section of the instrument. In addition, the data processing unit is in this case set up to take account of said relative position when calculating the corrections. The relative position represents a spatial condition which has to be met even by the corrected positions. Thus the quality of the correction can be improved by using this information. The relative position can be implicitly taken into account in the optimization of the (extended) quality dimension or alternatively in a separate correction step following an evaluation of the quality dimension.

In the context of the second alternative referred to above, the position of at least one localizer (pre-) corrected by the evaluation of the quality dimension is, in a preferred embodiment of the data processing device, further so corrected while taking account of the vascular layout according to the vascular map that the corrected final positions of the localizers likewise adopt the given relative position. Following the evaluation of the quality dimension, for instance, one of the corrected positions can be displaced along the vascular layout to maintain a preset distance from the other corrected position.

According to another further aspect, the data processing unit is set up to output a warning if the corrected position of the localizer implies an orientation and/or shape of the instrument section deviating by more than a preset limit value from the measured orientation and/or shape. As explained above, the orientation of the localizer or the instrument section is in many cases a signal which can be determined with a relatively high degree of certainty. If the difference between corrected and measured orientation is too large, this may indicate a potential problem. There may, for instance, be a risk that a catheter could injure or penetrate the wall of blood vessels.

The device further preferably includes means enabling the position of the localizer relative to the vascular map to be verified. By using these means, the actual position of the localizer in the vascular layout can be determined at least once. Such a verified result can then be used as a starting point for the subsequent correction of measured positions, taking account of the quality dimension.

The means referred to above may, in particular, comprise an imaging device, such as a (rotary) X-ray unit, an X-ray CT or a magnetic resonance tomograph. With such an imaging device, it is possible not only to verify the positions of the localizer, but also to generate vascular maps.

The invention further relates to a method for the determination of the position of an instrument in a vascular system with the aid of at least one localizer attached to the instrument and of a vascular map, said method comprising the following steps:
a) The measurement of the spatial position of the localizer and of the orientation and/or shape of an instrument section.
b) The correction of the measured spatial position while taking account of (optimizing) a quality dimension, the quality dimension including weighted components measuring on the one hand the deviation of the measured position of the localizer and on the other hand the deviation of the measured orientation and/or shape of the instrument section from the vascular layout according to the vascular map.

In its general form, the method comprises the steps which can be taken using a device of the type described above. With regard to details, advantages and further aspects of the method, the above description therefore applies.

According to a further aspect of the method, a spatially continuous transformation is determined on the basis of individual corrections calculated as described above. The spatially continuous transformation then permits the correction of measured position values at virtually any point.

These and other aspects of the invention are apparent from and will be elucidated with reference to the embodiments described hereinafter.

Figure 1:
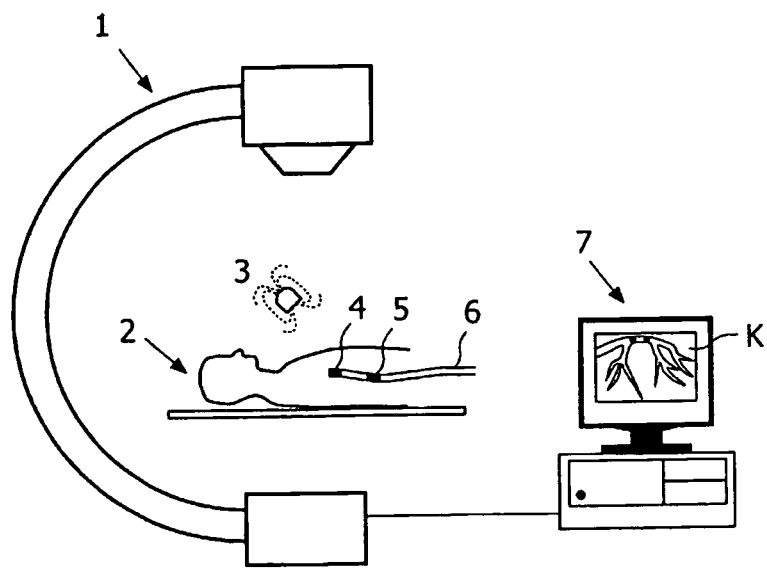
FIG. 1 is a diagrammatic representation of the structure of a device according to the invention for localizing a catheter.

In the diagrammatic representation of FIG. 1, the imaging device is recognizable as a C-shaped X-ray unit 1, by means of which two- or three-dimensional images of the body of a patient 2 can be generated. The application on which the present description is based is the examination of the coronary vessels of the patient 2 by means of a catheter 6. To prepare for such an examination, angiographic projections of the relevant vessels are first produced after injecting contrast agents and stored as (2D or 3D) vascular maps in the memory of a connected data processing unit 7 (workstation). In addition, the data processing unit may incorporate the usual computer components, such as central processor, volatile and non-volatile memory (RAM, hard disc, CD, . . . ) etc. It further includes suitable programs for the execution of the steps of data evaluation explained in greater detail below.

In order to limit the exposure of the patient (and the staff) to X-rays and contrast agents, there is no X-ray monitoring during the entire catheter examination. The current position of the catheter 6 is instead observed with the aid of active localizers 4, 5, whose spatial position (or coordinates) and orientation can be measured by an associated localizing device. In the illustrated case, this is an electromagnetic localizing device with a field generator 3 for generating a magnetic field inhomogeneous in time and space. The measuring signals of the magnetic field sensors 4, 5 attached to the tip of the catheter 6 as localizers allow a conclusion to be drawn with regard to their spatial position and orientation, because the magnetic field generated by the field generator 3 is known in principle. The measuring signals output by the localizers 4, 5 are transmitted to the data processing unit 7, where the positions of the localizers 4, 5 relative to a stored vascular map are derived from these signals. The vascular map K can then be displayed on a monitor 7 together with the detected positions to simplify the navigation of the catheter for the doctor.

The approach described above, however, has the disadvantage that the measured positions of the localizers 4, 5 are generally subject to major or minor inaccuracies. In the illustrated situation of a catheter laboratory, in particular, there is interference by field distortion mainly due to the image amplifier in the C-structure of the X-ray system 1.

Figure 2:
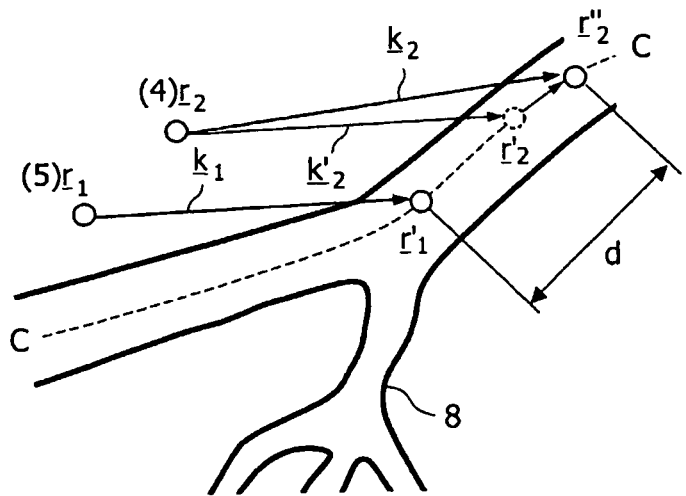
FIG. 2 illustrates the geometrical relationships at the correction of measured positions in a vascular layout according to the invention.

The problems described above, to which the measuring signals are subject, are illustrated in greater detail in FIG. 2. This shows the layout of a vessel 8 according to a vascular map, the center line C of the vessel being indicated by a broken line. The measured position $r_1$ of the proximal position sensor 5 or the measured position r) of the distal position sensor 4 respectively can be entered into the vascular map on the basis of known calibration parameters. In this context, it is assumed that a precise registration between the vascular map and the localizers 4, 5 can first be achieved (for instance by means of an X-ray image of the catheter). As the catheter is pushed further through the vessel, the leading localizer 4 will be the first to enter an area with a disturbed magnetic field, resulting in a correspondingly incorrect measured position. Experiments, however, have shown that the orientation of the localizers is affected relative little, typically by 1.5+/−2.2°.

The orientation can therefore be used as a relatively accurate measurement, by means of which the most probable "true" position of the catheter on the vascular map can be established. For a more detailed explanation, the measured positions $r_1$, $r_2$ are shown outside the vascular layout in FIG. 2 as a result of the interference explained above. Since this position cannot be correct, the measured values have to be corrected.

Instead of transposing the measured positions $r_1$, $r_2$ into the vascular layout of the map via the shortest possible route, a more differentiated procedure is adopted here. Two correction vectors $k_1$ and $k_2'$ are calculated to convert the measured positions $r_1$ and $r_2$ to corrected positions $r_1'$ or $r_2'$ respectively. The calculation of these correction vectors $k_1$, $k_2'$ is accompanied by the optimization of a quality dimension Q, which takes into account both the distance of the measured positions $r_1$, $r_2$ from the vascular layout and the measured orientation of the localizers or between the localizers. The orientation between the localizers is determined by the difference $(r_2-r_1)$ of the measured positions (apart from an eventual standardization). A typical quality dimension Q fulfilling the conditions explained above is, for instance, specified by the function $$Q = Q(\rho_1, \rho_2) = w_1((r_1-\rho_1)^2 + (r_2-\rho_2)^2) + w_2((r_2-r_1)-(\rho_2-\rho_1))^2$$

with $w_1$, $w_2$ being weighting factors presettable by the user, typical values being, for example, $w_1 \in [0;1]$ and $w_2 \in ]0;1]$. The position vectors $\rho_1$ and $\rho_2$ are arbitrary vectors from the vascular layout. The position vectors $\rho_1 = r_1'$ and $\rho_2 = r_2'$ for which Q assumes a minimum, represent the required corrected values for $r_1$ and $r_2$. With these, the associated correction vectors $k_1 = r_1' - r_1$ and $k_2' = r_2' - r_2$ are also known.

In another formulation of the quality dimension Q, the second term could additionally or alternatively include components which take account of (individual) orientations directly measured by the localizers. In addition or as an alternative, Q could include a component evaluating the form error between the measured course of the catheter and the vascular layout according to the vascular map. The course of the catheter could, for instance, be determined from the measured positions of a plurality (e.g. four) localizers by adapting a catheter model (e.g. a spline function), and Q could contain the integral of the difference between the course of the catheter and the vascular layout.

As the case illustrated in FIG. 2 shows, the inclusion of orientation (factor $w_2$) in the quality dimension Q has the result that the measured positions $r_1$, $r_2$ are directionally displaced into a section of the vascular layout, the orientation of which corresponds to the measured orientation $(r_2-r_1)$.

A further correction step can be taken optionally. By calculating the positions $r_1'$ and $r_2'$ or the correction vectors $k_1$ and $k_2'$ respectively as described above, only a—as such relatively precise—lateral correction has been achieved relative to the vascular layout. The positional correction in the longitudinal direction of the vessel, on the other hand, remains fairly inaccurate, because the measured orientation data are subject to fuzziness and the orientation data from the vascular map are subject to tolerances. This can result in some significant errors in parts of the vascular map, in particular at points where the curvature of the vessel is relatively small.

In order to correct a position in the longitudinal direction of the vascular layout (along the center line C of the vessel), the fact that the two localizers 4, 5 are located on the catheter 6 at a constant distance d from one another is used. The (pre-corrected) position $r_2'$ of the leading localizer 4 is moved along the center line C of the vessel until its distance from the (pre-corrected) position $r_1'$ of the other localizer 5 is equal to the preset constant distance d. This procedure results in the final corrected position $r_2''$ for the leading localizer 4, from which the final correction vector $k_2 = r_2'' - r_2$ can then be determined. The resulting correction vectors $k_1$ and $k_2$ can then be stored (as a function of the associated positions $r_1$ and $r_2$).

If the angle between the final corrected orientation $(r_2'' - r_1')$ and the measured orientation $(r_2 - r_1)$ exceeds a preset value, the data processing device 7 can output a visual or audible warning to the user to warn him of a potential risk of injury to or penetration of the wall of the vessel.

The correction method explained above for two measured positions $r_1$, $r_2$ can further be used for the local calculation of a continuous transformation map in the relevant area of the vascular layout. The distance between the calculated reference point $r_1$, $r_2$ for the correction vectors $k_1$, $k_2$ can be treated as a parameter to be set by the user, which is in particular selected in accordance with the minimum length scale on which the interference field fluctuates. The selected distance d of the localizers 4, 5 on the catheter 6 should depend on the length scale of the field interference as well.

With suitable methods of interpolation or extrapolation, a dense transformation map for the entire relevant volume of the vascular system can be calculated from the measured reference points. This transformation can be refreshed with each newly obtained measured value. In this way, the method can be adapted even to slowly fluctuating interference. Faster changes to the interference field, on the other hand, are preferably dealt with by simply restarting the process described above with a renewed initial registration between the catheter 6 and the vascular layout.

The invention claimed is:

1. A device for determining a position of an instrument in a vascular system, comprising:
    two localizers fitted to the instrument, each of the localizers incorporating a magnetic field sensor configured to measure a plurality of spatial positions of the localizers used to determine an orientation of the instrument and/or a shape of a section of the instrument between the two localizers;
    a memory to store a vascular map representing a vascular layout of the vascular system in which the instrument is positioned; and
    a processor configured to correct the measured plurality of spatial positions of the localizers taking into account a distance of the spatial positions from the vascular layout represented on the vascular map, a difference between the spatial positions of the two localizers, and a quality dimension including a first weighted component indicating a deviation of the measured plurality of spatial positions of the two localizers from the vascular layout as represented by the vascular map, and a second weighted component indicating a deviation of the measured orientation of the instrument and/or shape of the section from the vascular layout as represented by the vascular map.

2. The device as claimed in claim 1, wherein the processor is further configured to calculate a locally continuous transformation from respective corrections of the plurality of spatial positions.

3. The device as claimed in claim 1, wherein the localizers are attached to the instrument in a known relative position used to correct the measured plurality of spatial positions.

4. The device as claimed in claim 3, wherein the quality dimension is used in accordance with the vascular layout, so that the corrected plurality of spatial positions adopt the known relative position.

5. The device as claimed in claim 1, wherein the processor is further configured to output a warning if the corrected plurality of spatial positions includes one of an orientation of the instrument and/or a shape of the section of the instrument that deviates by more than a preset limit value from the indicating orientation of the instrument and/or shape of the section.

6. The device as claimed in claim 1, wherein the plurality of spatial positions relative to the vascular layout is verified.

7. The device according to claim 1, further comprising an imaging device configured to generate the vascular map.

8. A method for determining a position of an instrument in a vascular system, the method comprising acts of:
providing two localizers attached to the instrument each of the localizers incorporating a magnetic field sensor and a vascular map representing a vascular layout of the vascular system in which the instrument is positioned
measuring a plurality of spatial position of the localizers;
determining an orientation of the instrument and/or shape of a section of the instrument between at least two localizers; and
correcting the measured plurality of spatial positions using a distance of the spatial positions from the vascular layout represented on the vascular map, a difference between the spatial positions of the two localizers, and a quality dimension including a first weighted component indicating of a deviation of the measured plurality of spatial positions of the two localizers from the vascular layout as represented by the vascular map, and a second weighted component indicating a deviation of the measured orientation of the instrument and/or shape of the section from the vascular layout as represented by the vascular map.

9. The method as claimed in claim 8, comprising an act of calculating a spatially continuous transformation on the basis of a plurality of corrections.

* * * * *